United States Patent
Berg-Slot et al.

(10) Patent No.: US 9,029,283 B2
(45) Date of Patent: May 12, 2015

(54) CATALYST COMPOSITION, ITS PREPARATION AND USE

(75) Inventors: Johanna Jacoba Berg-Slot, Amsterdam (NL); László Domokos, Amsterdam (NL); Ingrid Maria Van Vegchel, Amsterdam (NL)

(73) Assignee: Shell Oil Company, Houston, TX (US)

( * ) Notice: Subject to any disclaimer, the term of this patent is extended or adjusted under 35 U.S.C. 154(b) by 590 days.

(21) Appl. No.: 12/671,086

(22) PCT Filed: Jul. 28, 2008

(86) PCT No.: PCT/EP2008/059850
§ 371 (c)(1),
(2), (4) Date: Jun. 1, 2010

(87) PCT Pub. No.: WO2009/016143
PCT Pub. Date: Feb. 5, 2009

(65) Prior Publication Data
US 2010/0249479 A1   Sep. 30, 2010

(30) Foreign Application Priority Data

Jul. 31, 2007  (EP) .................................... 07113575

(51) Int. Cl.
| | | |
|---|---|---|
| *B01J 29/06* | (2006.01) | |
| *B01J 29/44* | (2006.01) | |
| *B01J 29/40* | (2006.01) | |
| *B01J 37/00* | (2006.01) | |
| *B01J 23/62* | (2006.01) | |
| *C07C 4/18* | (2006.01) | |

(52) U.S. Cl.
CPC ............... *B01J 29/44* (2013.01); *B01J 29/405* (2013.01); *B01J 37/0009* (2013.01); *B01J 23/626* (2013.01); *B01J 2229/20* (2013.01); *B01J 2229/42* (2013.01); *C07C 4/18* (2013.01)

(58) Field of Classification Search
USPC .................. 502/60, 63, 64.66, 71, 73, 74, 77
See application file for complete search history.

(56) References Cited

U.S. PATENT DOCUMENTS

| | | | |
|---|---|---|---|
| 3,702,886 A | 11/1972 | Argauer et al. ............... 428/328 |
| 3,992,468 A | 11/1976 | Cosyns et al. ............ 260/672 R |
| 4,088,605 A | 5/1978 | Rollmann ...................... 252/455 |
| 4,331,822 A * | 5/1982 | Onodera et al. .............. 585/482 |
| 4,511,547 A | 4/1985 | Iwayama et al. ............. 423/329 |
| 5,157,191 A | 10/1992 | Bowes et al. ................. 585/533 |
| 5,227,557 A * | 7/1993 | Bournonville et al. ....... 585/419 |
| 5,242,676 A | 9/1993 | Apelian et al. ................ 423/714 |
| 5,567,666 A * | 10/1996 | Beck et al. ....................... 502/71 |
| 5,689,027 A | 11/1997 | Abichandani et al. ........ 585/481 |
| 6,245,704 B1 * | 6/2001 | Benazzi et al. .................. 502/74 |
| 6,465,705 B1 * | 10/2002 | Merlen et al. ................. 585/481 |
| 6,635,792 B2 | 10/2003 | Choi et al. |
| 6,949,181 B2 | 9/2005 | Remans et al. ................. 208/27 |

FOREIGN PATENT DOCUMENTS

| | | | |
|---|---|---|---|
| CN | 1364099 A | 7/2000 | .............. B01J 37/00 |
| CN | 1478139 | 11/2001 | ............ C10G 45/64 |
| EP | 18498 | 11/1980 | ............... C07C 5/27 |
| EP | 425712 | 5/1991 | ............... C07C 5/22 |
| JP | 6056710 | 3/1994 | ............ B01J 27/135 |
| WO | WO0003884 | 1/2000 | .............. B60J 10/00 |
| WO | WO0038834 | 7/2000 | .............. B01J 29/22 |
| WO | WO2007037866 | 5/2007 | .............. B01J 29/06 |

OTHER PUBLICATIONS

Journal of Catalysis vol. 210, pp. 431-444, (2002).

* cited by examiner

*Primary Examiner* — Elizabeth Wood
(74) *Attorney, Agent, or Firm* — Charles W. Stewart

(57) ABSTRACT

A catalyst composition which comprises: a) a carrier which comprises at least 30 wt % of a binder selected from silica, zirconia and titania; at least 20 wt % of a pentasil zeolite, having a bulk silica to alumina ratio in the range of from 20 to 150 and being in its $H^+$ form; and less than 10 wt % of other components, all percentages being on the basis of total carrier; b) platinum in an amount in the range of from 0.001 to 0.1 wt %, on the basis of total catalyst; and c) tin in an amount in the range of from 0.01 to 0.5 wt %, on the basis of total catalyst; its preparation and use; are provided.

18 Claims, No Drawings

CATALYST COMPOSITION, ITS PREPARATION AND USE

The present application claims priority from European Patent Application 07113575.0 filed 31 Jul. 2007.

FIELD OF THE INVENTION

The present invention relates to a catalyst composition, its preparation, and its use in ethylbenzene dealkylation.

BACKGROUND OF THE INVENTION

Ethylbenzene is one of the aromatic hydrocarbons that is obtained from naphtha pyrolysis or in reformate. Reformate is an aromatic product given by the catalysed conversion of straight-run hydrocarbons boiling in the 70 to 190° C. range, such as straight-run naphtha. Such hydrocarbons are themselves obtained by fractionation or distillation of crude petroleum oil, their composition varying depending on the source of the crude oil, but generally having a low aromatics content. On conversion to reformate, the aromatics content is considerably increased and the resulting hydrocarbon mixture becomes highly desirable as a source of valuable chemicals intermediates and as a component for gasoline. The principle components are a group of aromatics often referred to as BTX: benzene, toluene, and the xylenes, including ethylbenzene. Other components may be present such as their hydrogenated homologues, e.g. cyclohexane.

Of the BTX group the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity and xylene isomerisation or transalkylation processes have been developed to increase the proportion of para-xylene.

A further process that the gasoline producer can utilize is the hydrodealkylation of ethylbenzene to benzene.

Generally, the gasoline producer will isolate BTX from the reformate stream, and then subject the BTX stream to xylene isomerisation with the aim of maximising the para-xylene component. Xylene isomerisation is a catalytic process; some catalysts used in this process have the ability not just to isomerise xylenes but also simultaneously to dealkylate the ethylbenzene component. Normally the para-xylene is then separated out to leave benzene, toluene (unless toluene conversion processes have already been applied) and the remaining mixed xylenes, including ethylbenzene. This BTX stream can either be converted by transalkylation to increase the yield of xylenes by contacting with a heavier hydrocarbon steam or can be converted by dealkylation to eliminate selectively ethylbenzene and to increase the yield of benzene, while allowing the xylenes to reach equilibrium concentrations. The latter process is the subject of the present invention.

In ethylbenzene dealkylation at this latter stage of BTX treatment, it is a primary concern to ensure not just a high degree of conversion to benzene but also to avoid xylene loss. Xylenes may typically be lost due to transalkylation, e.g. between benzene and xylene to give toluene, or by addition of hydrogen to form, for example, alkenes or alkanes.

It is therefore the aim of the present invention to provide a catalyst that will convert ethylbenzene to benzene with a high selectivity without xylene loss. Simultaneous xylene isomerisation to equilibrium concentrations is also desirable.

The catalysts used for the production of reformate are often platinum-on-alumina catalysts. For the conversion of BTX streams to increase the proportion of closely configured molecules, a wide range of proposals utilizing zeolitic catalysts have been made, which include those of EP-A-0 018 498, EP-A-0 425 712, and WO 00/38834.

European Patent Specification No. 0 018 498 A1 is concerned with catalysts suitable for xylene isomerisation and the simultaneous dealkylation of ethylbenzene and reviews a number of earlier proposals for the use of platinum ZSM-series zeolitic catalysts. Generally such catalysts are shown to have a superior activity in isomerising xylenes and to dealkylate ethylbenzene, but are required to be used at high temperatures as there is a tendency for platinum to hydrogenate the benzene ring and to cause other undesirable side-reactions such as disproportionation and transalkylation at the low temperatures that are preferred for xylene isomerisation. The proposal of EP-A-0 018 498 is to use a second metal, which is preferably tin, barium, titanium, indium and cadmium, in combination with platinum and a high-silica zeolite bound with a refractory inorganic oxide, which in all of the examples is alumina.

EP-A-0 425 712 describes an improved catalyst for simultaneous xylene isomerisation and ethylbenzene dealkylation, which is formed by combining a group VIII metal, preferably platinum, with a lead component, and a halogen component, on a carrier of a pentasil zeolite and an inorganic oxide binder, preferably alumina, such that a specific ratio of lead to Group VIII metal is achieved and such that the bulk of the Group VIII and lead components are combined with the binder material.

WO 00/38834 describes a mixed zeolitic catalyst for the disproportionation and transalkylation of aromatic hydrocarbons. That catalyst consists of a carrier of 10 to 80 wt % mordenite and/or zeolite beta, 0 to 70 wt % ZSM-5, and 5 to 90 wt % inorganic binder, plus a metal component of platinum with either tin or lead. While the binder is said to be most preferably alumina or silica, only alumina-bound catalysts are exemplified.

There are fewer proposals for catalysts directed solely for the hydrodealkylation of aromatics.

Toppi et al in Journal of Catalysis 210, 431-444 (2002) studies the use of silica-supported platinum and platinum-tin catalysts in comparison with acidic catalysts of just alumina and chlorinated alumina, on the hydrodealkylation of n-propylbenzene, and finds that the formation rate of benzene was the highest for the acidic catalysts.

U.S. Pat. No. 3,992,468 proposes two catalysts for the hydrodealkylation of alkylaromatic hydrocarbons: catalyst A essentially containing a) a carrier, b) at least one metal selected from the group consisting of the metals from group VIII and c) at least one metal selected from the group consisting of zinc, cadmium, gallium, indium, thallium, copper, silver, gold, yttrium, titanium, niobium, tantalum, and manganese; and catalyst B essentially containing a) a carrier, b) at least one metal selected from a first group consisting of chromium, molybdenum, tungsten, rhenium, and manganese, and c) at least one additional metal different to that of the first group and being selected from the metals of the first group plus copper, silver, gold, zinc, cadmium, gallium, indium, thallium, germanium, tin and lead, each metal being in an amount of from 0.05 to 20 wt %. The carrier is selected from among known carriers, for example, alumina, magnesia, magnesia-silica, acidic alumina, chlorinated and/or fluorinated alumina, alumina-silica, zirconia, zirconia-silica, and molecular sieves or zeolites, and is preferably alumina.

SUMMARY OF THE INVENTION

The present invention provides a catalyst composition which comprises a) a carrier which comprises at least 30 wt % of a binder selected from silica, zirconia and titania; at least 20 wt % of a pentasil zeolite, having a bulk silica to alumina ratio in the range of from 20 to 150 and being in its H$^+$ form; and less than 10 wt % of other components, all percentages being on the basis of total carrier;
b) platinum in an amount in the range of from 0.001 to 0.1 wt %, on the basis of total catalyst; and
c) tin in an amount in the range of from 0.01 to 0.5 wt %, on the basis of total catalyst.

The present invention also provides a process for the preparation of the catalyst, which comprises combining at least 30 wt % of a binder selected from silica, zirconia and titania, at least 20 wt % of a pentasil zeolite, and less than 10 wt % of an optional other component, shaping the resulting mixture, if desired, and compositing with in the range of from 0.001 to 0.1 wt % of platinum, and in the range of from 0.01 to 0.5 wt % of tin.

Also provided is an ethylbenzene dealkylation process which comprises contacting in the presence of hydrogen a feedstock which comprises ethylbenzene, preferably one comprising $C_7$ to $C_9$ aromatics, including xylenes and ethylbenzene, with a catalyst composition of the present invention.

DETAILED DESCRIPTION OF THE INVENTION

The catalyst composition of the present invention has been found to show a higher benzene selectivity combined with reduced xylene losses for an equal activity and benzene purity compared with analogous catalysts which utilize alumina-bound zeolite, alumina being the preferred binder of the prior art catalysts.

Silica is preferably used as a binder in the catalyst composition of the present invention and may be a naturally occurring silica or may be in the form of a gelatinous precipitate, sol or gel. The form of silica is not limited and the silica may be in any of its various forms: crystalline silica, vitreous silica or amorphous silica. The term amorphous silica encompasses the wet process types, including precipitated silicas and silica gels, or pyrogenic or fumed silicas. Silica sols or colloidal silicas are non-settling dispersions of amorphous silicas in a liquid, usually water, typically stabilized by anions, cations, or non-ionic materials.

The silica binder preferably is a mixture of two silica types, most preferably a mixture of a powder form silica and a silica sol. Conveniently powder form silica has a B.E.T. surface area in the range of from 50 to 1000 m$^2$/g; and a mean particle size in the range of from 2 nm to 200 μm, preferably in the range of from 2 to 100 μm, more preferably 2 to 60 μm, especially 2 to 10 μm as measured by ASTM C 690-1992 or ISO 8130-1. A very suitable powder form silica material is Sipernat 50, a white silica powder having predominantly spherical particles, available from Degussa (Sipernat is a trade name). A very suitable silica sol is that sold under the trade name of Bindzil by Eka Chemicals. Where the mixture comprises a powder form silica and a silica sol, then the two components may be present in a weight ratio of powder form to sol form in the range of from 1:1 to 10:1, preferably 2:1 to 5:1, more preferably from 2:1 to 3:1. The binder may also consist essentially of just the powder form silica.

Where a powder form of silica is used as a binder in the catalyst composition of the present invention, preferably a small particulate form is utilized, which has a mean particle size in the range of from 2 to 10 μm as measured by ASTM C 690-1992. An additional improvement in carrier strength is found with such materials. A very suitable small particulate form is that available from Degussa under the trade name Sipernat 500LS.

Preferably the silica component is used as a pure silica and not as a component in another inorganic oxide. It is most preferred that the silica and indeed the carrier, is essentially free of any other inorganic oxide binder material, and especially is free of alumina. At most only a maximum of 2 wt % alumina, based on the total carrier, is present.

In preferred embodiments which utilize a surface modification dealumination treatment, the presence of alumina can particularly be detrimental since with an alumina carrier the surface modification would detrimentally affect the physical integrity of the carrier.

Pentasil zeolites are well known to the skilled person. 'Pentasil' is a term used to describe a class of shape-selective zeolites which are typically characterized by a silica to alumina ratio (SAR) of at least 12 and are constructed of five-membered rings (their framework being built up from 5-1 secondary building units). The pentasil zeolite utilized in the present invention has a SAR in the range of from 20 to 150. The SAR is the bulk or overall silica/alumina ratio which may or may not be different to the framework SAR depending on any treatment to which the zeolite, either when free or in catalyst form, has been subjected.

Of the pentasil zeolites, the preferred zeolites are ZSM-5, ZSM-8, ZSM-11, ZSM-12, TON, e.g. ZSM-22, ZSM-23, ZSM-35, e.g. ferrierite, and ZSM-48, with those having the MFI configuration, and especially ZSM-5, being the most preferred. All of these zeolites are well known and documented in the literature, see for example the Database of Zeolite Structures: http://www.iza-structure.org/databases/ or Baerlocher et al "Atlas of zeolite framework types", 5$^{th}$ revised edition (2001), published on behalf of the Structure Commission of the International Zeolite Association, by Elsevier. Pentasil zeolites are reviewed in the Database at http://www.iza-structure.org/databases/Catalog/Pentasil-s.pdf.

Such zeolites can exist in various forms depending on the ion present at the cation sites in the zeolite structure. Generally the available forms contain an alkali metal ion, an alkaline earth metal ion, or a hydrogen or hydrogen precursor ion at the cation site. In the catalyst composition of the present invention, the zeolite is present in the form containing hydrogen or hydrogen precursor; this form is commonly known as the H$^+$ form. The zeolite may be used either in its template-free or its template-containing form. Some advantage in reduction of xylene loss has been found where the template-containing form is used during the preparation.

The SAR of such zeolites is preferably at least 25, most preferably at least 30, and is preferably at most 100, most preferably at most 90, especially at most 50.

The zeolite starting material can exist in a number of particle size ranges. Suitably the zeolite has a primary particle diameter in the range of from 20 nm to 10 μm. Useful catalysts have been prepared using a large crystal size ZSM-5 zeolite having an average crystallite size in the range of from 1 to 10 μm, and also using a small particle size ZSM-5 having a primary particle diameter below 200 nm. Generally, in terms of particle size distributions, the ZSM-5 may have a particle size distribution in which the diameter of 50% of the particles, D(v, 0.5), is greater than 2 μm and that of 90% of the particles, D(v, 0.9), is less than 30 μm.

Suitable ZSM-5 materials can be prepared by procedures documented in the literature, for example in U.S. Pat. No. 3,702,886, in references provided in the Atlas, or Database, of Zeolite Structures, and in other literature references such as by Yu et al in Microporous and Mesoporous Materials 95 (2006) 234 to 240, and Iwayama et al in U.S. Pat. No. 4,511,547.

Suitable grades of ZSM-5 zeolite include CBV 3014E, CBV 8014, and CBV 3020E, available commercially from Zeolyst International.

The zeolite is an important factor in the activity and selectivity properties shown by the catalyst composition of the invention. There is a balance between the activity and selectivity desired which may result in a different optimum zeolite content in the carrier depending on the zeolite used and the SAR of the zeolite used. Generally a higher zeolite content may in some cases be advantageous to produce a higher activity from the catalyst composition, while a lower zeolite content may provide a higher selectivity.

It has been found that when using a ZSM-5 zeolite of SAR 40, reduction of the zeolite content gives rise to an increased benzene selectivity with lower xylene losses but for a penalty of a lower activity, as shown by a higher temperature required to provide the same level of conversion of ethylbenzene. Where a higher SAR zeolite is utilized it is necessary to increase the proportion of zeolite in the catalyst carrier to achieve optimum performance.

While this balance may cause a different optimum depending on the conditions utilized in the ethylbenzene dealkylation process, generally it is preferred to minimize the amount of zeolite used in the catalyst carrier, since a higher amount of zeolite may negatively affect the physical properties of the catalyst carrier such as lowering its strength. It is generally preferred that the carrier is composed of in the range of from 30 to 80 wt %, most preferably from 50 to 70 wt %, silica and in the range of from 20 to 70 wt %, most preferably from 30 to 50 wt %, zeolite.

A very suitable catalyst carrier for the present invention contains a pentasil zeolite, especially ZSM-5, having a SAR in the range of from 20 to 50, especially 30 to 40, in an amount in the range of from 20 to 50 wt %, especially 25 to 40 wt %.

Preferably there is no other component than binder, preferably silica, and pentasil zeolite in the carrier. However it is possible to include up to 10 wt % of other components whilst still obtaining the benefits of the present invention. Such other components may be selected from other refractory inorganic oxide binder materials and other zeolites. Other binder materials may be alumina, and magnesia. Examples of other zeolites are 8, 10, or 12-membered ring zeolites, for example mordenite, and zeolite beta, and acidic mesoporous materials such as the MCM-series of zeolites, e.g. MCM-22 and MCM-41.

The carrier is conveniently a shaped carrier and may be treated to enhance the activity of the zeolite component. It has been found advantageous to perform a surface modification, such as is described in U.S. Pat. No. 6,949,181.

Modification of the molecular sieve reduces the mole percentage of alumina which basically implies that the number of acid sites is reduced. This can be achieved in various ways. A first way is applying a coating of a low acidity inorganic refractory oxide onto the surface of the crystallites of the molecular sieve. Suitable inorganic oxides for this purpose are silica, zirconia or titania, of which silica is preferred. By applying such coating onto the crystallites' surface, the total number of oxide moieties in the modified molecular sieve (i.e. the original molecular sieve plus the coating) is increased, whilst the number of alumina moieties remains the same, thus resulting in a reduced mole percentage of alumina. A major advantage of this method is that the number of acid sites on the surface of the crystallites of the molecular sieve is drastically reduced to essentially nil.

Another very useful way of modifying the molecular sieve is by subjecting it to a dealumination treatment. In general, dealumination of the crystallites of a molecular sieve refers to a treatment, whereby aluminum atoms are either withdrawn from the molecular sieve framework leaving a defect or are withdrawn and replaced by other atoms, such as silicon, titanium, boron, germanium or zirconium. Dealumination can be attained by methods known in the art. Particularly useful methods are those, wherein the dealumination selectively occurs, or is claimed to occur selectively, at the surface of the crystallites of the molecular sieve. In this way, namely, the same effect as with the coated molecular sieves can be attained: the number of acid sites at the surface of the crystallites is reduced.

In U.S. Pat. No. 5,157,191 a very suitable process for dealuminating the surface of an aluminosilicate zeolite is described wherein the zeolite is contacted with an aqueous solution of a hexafluorosilicate salt, most advantageously ammonium hexafluorosilicate (AHS), to extract the aluminum atoms located at the surface of the zeolite and replace these atoms with silicon atoms. In said U.S. patent several hydrocarbon conversion reactions including shape-selective oligomerization of olefins to produce high viscosity lube oils, cracking, isomerization of xylene, disproportionation of toluene and alkylation of aromatics, are described in which the surface modified zeolite could be useful as a catalyst.

Another method for dealuminating the surface of zeolite crystallites is disclosed in U.S. Pat. No. 5,242,676. According to this method a zeolite is contacted with a dicarboxylic acid, suitably in the form of an aqueous solution, for sufficient time to effect at least 40% reduction in surface acidity with less than 50% overall dealumination. A very suitable dicarboxylic acid is oxalic acid, whilst suitable zeolites should have a Constraint Index of greater than 1 and include ZSM-5, ZSM-11, ZSM-23, and ZSM-35.

Yet another method for obtaining a zeolite having a dealuminated outer surface is disclosed in U.S. Pat. No. 4,088,605. According to this "in situ dealumination" method a zeolite having an aluminium-free outer shell of silica is produced by a two stage method comprising (i) initiating crystallization in a crystallization medium to form the zeolite and (ii) altering the crystallization medium to substantially eliminate the aluminum therein, suitably by adding a complexing agent to the crystallization mixture which forms a complex with the aluminum ions present, after which the complex formed is removed. Examples of suitable complexing agents are gluconic acid, tartaric acid and ethylenediamine-tetraacetic acid (EDTA). Zeolites having an aluminum-free outer shell which can be produced in this manner include ZSM-5 and ZSM-35.

Of the (surface) dealumination methods described above, the method involving the treatment with a hexafluorosilicate, most suitably ammoniumhexa-fluorosilicate (AHS), has been found to offer an additional advantage. Treatment of the aluminosilicate zeolite extrudates with AHS, which extrudates are obtained by extruding the zeolite with or without binder, has been found to result in the extrudates also having an increased mechanical strength in addition to the expected dealuminated outer surface. This increase in mechanical strength occurs particularly for extrudates obtained by extruding the zeolite with a silica binder.

The dealumination of the aluminosilicate zeolite results in a reduction of the number of alumina moieties present in the zeolite and hence in a reduction of the mole percentage of alumina. A very good measure for the reduction of the mole percentage of alumina is the increase of the silica to alumina ($SiO_2/Al_2O_3$) molar ratio of the zeolite as a result of the dealumination treatment. For the purpose of the present invention, the dealumination ratio, which is defined as the ratio of $SiO_2/Al_2O_3$ molar ratio of surface dealuminated zeolite (i.e. after dealumination) to $SiO_2/Al_2O_3$ molar ratio of starting zeolite (i.e. before dealumination), is suitably in the range of from 1.1 to 3.0, preferably from 1.3 to 2.5 and even more preferably from 1.5 to 2.2. Selective dealumination of the surface of the zeolite crystallites, accordingly, also results in a reduction of the number of surface acid sites of the zeolite crystallites, whilst not affecting the internal structure of the zeolite crystallites. The extent of dealumination of the surface of the crystallites depends on the severity of the dealumination treatment. Suitably, the number of surface acid sites of the zeolite is reduced with at least 70%, preferably with at least 80% and even more preferably with at least 90%. In a most preferred embodiment the number of surface acid sites is reduced with essentially 100% by the selective dealumination, thus leaving essentially no surface acid sites at all.

The surface modification may be applied just once to the carrier or may be applied two or more times. However we have not found any advantage in repeated application. The concentration of the AHS treatment does however appear to have an effect. Preferably the concentration of active ingredient (AHS) is in the range of from 0.005 to 0.5M. Preferably the concentration is in the range of from 0.01 to 0.2M, more preferably 0.01 to 0.05M, and especially 0.01 to 0.03M, which has been found to provide a catalyst composition having an increased activity.

For the avoidance of doubt, where a surface modification treatment has occurred that leaves silicon on the surface of the carrier, and where silica is used as a binder, this silicon content, which is usually only a small quantity, does not form part of the silica content of the carrier according to the invention.

In shaped form, for example as extrudates, the carrier generally has a B.E.T. surface area falling in the range of from 100 to 400 $m^2/g$, preferably 130 to 300 $m^2/g$, more preferably 150 to 250 $m^2/g$; and a pore volume, by mercury intrusion, in the range of from 0.2 to 1.2 ml/g, preferably 0.4 to 1.0 ml/g, more preferably 0.5 to 0.9 ml/g. The flat plate crush strength generally is at least 50 $N·cm^{-1}$, preferably at least 70 $N·cm^{-1}$, and more preferably at least 80 $N·cm^{-1}$. It is generally, for example, of the order of 50 to 300 $N·cm^{-1}$, preferably 70 to 250 $N·cm^{-1}$, more preferably 80 to 200 $N·cm^{-1}$.

The catalyst composition of the invention also contains metal components in the form of platinum and tin. The platinum component is present in an amount in the range of from 0.001 to 0.1 wt %, based on total catalyst, and the tin component in an amount in the range of from 0.01 to 0.5 wt %, based on total catalyst. Most suitably the platinum component is present in an amount in the range of from 0.01 to 0.1, preferably 0.01 to 0.05, wt %. The tin component is most suitably present in an amount in the range of from 0.1 to 0.5, preferably 0.2 to 0.5, wt %.

The catalyst composition of the invention has properties similar to that of the carrier in B.E.T. surface area, pore volume and flat plate crush strength.

The catalyst composition of the present invention may be prepared using standard techniques for combining the zeolite, binder such as silica, and optional other carrier components; shaping; compositing with the metals components; and any subsequent useful process steps such as drying, calcining, and reducing.

The shaping may be into any convenient form such as powders, extrudates, pills and granules. Preference is given to shaping by extrusion. To prepare extrudates, commonly the pentasil zeolite will be combined with the binder, preferably silica, and if necessary a peptizing agent, and mixed to form a dough or thick paste. The peptizing agent may be any material that will change the pH of the mixture sufficiently to induce deagglomeration of the solid particles. Peptising agents are well known and encompass organic and inorganic acids, such as nitric acid, and alkaline materials such as ammonia, ammonium hydroxide, alkali metal hydroxides, preferably sodium hydroxide and potassium hydroxide, alkali earth hydroxides and organic amines, e.g. methylamine and ethylamine. Ammonia is a preferred peptizing agent and may be provided in any suitable form, for example via an ammonia precursor. Examples of ammonia precursors are ammonium hydroxide and urea. It is also possible for the ammonia to be present as part of the silica component, particularly where a silica sol is used, though additional ammonia may still be needed to impart the appropriate pH change. The amount of ammonia present during extrusion has been found to affect the pore structure of the extrudates which may provide advantageous properties. Suitably the amount of ammonia present during extrusion may be in the range of from 0 to 5 wt % based on the total dry mixture, preferably 0 to 3 wt %, more preferably 0 to 1.9 wt %, on dry basis.

The metals emplacement onto the formed carrier may be by methods usual in the art. The metals can be deposited onto the carrier materials prior to shaping, but it is preferred to deposit them onto a shaped carrier.

Pore volume impregnation of the metals from a metal salt solution is a very suitable method of metals emplacement onto a shaped carrier. The metal salt solutions may have a pH in the range of from 1 to 12. The platinum salts that may conveniently be used are chloroplatinic acid and ammonium stabilized platinum salts. Examples of suitable tin salts utilized are stannous (II) chloride, stannic (IV) chloride, stannous sulphate, and stannous acetate. The metals may be impregnated onto the shaped carrier either sequentially or simultaneously. Where simultaneous impregnation is utilized the metal salts used must be compatible and not hinder the deposition of the metals. It has been found useful to utilize a complexing or chelating agent in a combined platinum/tin salt solution to prevent unwanted metals precipitation. Examples of suitable complexing agents are EDTA (ethylenediamine tetraacetic acid), and derivatives thereof, HEDTA (N-(2-hydroxyethyl)ethylenediamine-N,N',N'-triacetic acid), EGTA (ethylene glycol-bis(2-aminoethylether)-N,N,N',N'-tetraacetic acid), DTPA (diethylene tridiamine pentaacetic acid), and NTA (nitrilotriacetic acid). Where EDTA is used, it is conveniently used in a molar ratio to tin of from 0.1 to 3, especially 1 to 2.

After shaping of the carrier, and also after metals impregnation, the carrier/catalyst composition is suitably dried, and calcined. Drying temperatures are suitably 50 to 200° C.; drying times are suitably from 0.5 to 5 hours. Calcination temperatures are very suitably in the range of from 200 to 800° C., preferably 300 to 600° C. For calcination of the carrier, a relatively short time period is required, for example 0.5 to 3 hours. For calcination of the catalyst composition, it may be necessary to employ controlled temperature ramping at a low rate of heating to ensure the optimum dispersion of the metals: such calcination may require from 5 to 20 hours.

Prior to use, it is necessary to ensure that the metals on the catalyst composition are in metallic (and not oxidic) form. Accordingly, it is useful to subject the composition to reducing conditions, which are, for example, heating in a reducing atmosphere, such as in hydrogen optionally diluted with an inert gas, or mixture of inert gases, such as nitrogen and carbon dioxide, at a temperature in the range of from 150 to 600° C. for from 0.5 to 5 hours.

The catalyst composition of the invention finds especial use in the selective dealkylation of ethylbenzene.

The ethylbenzene feedstock most suitably originates directly from a reforming unit or naphtha pyrolysis unit or is the effluent of a xylene isomerisation unit. Such feedstock usually comprises $C_7$ to $C_9$ hydrocarbons, and in particular one or more of o-xylene, m-xylene, p-xylene, toluene, and benzene in addition to ethylbenzene. Generally the amount of ethylbenzene in the feedstock is in the range of from 0.1 to 50 wt % and the total xylene content is typically at least 20 wt %. Typically the xylenes will not be in a thermodynamic equilibrium, and the content of p-xylene will accordingly be lower than that of the other isomers.

The feedstock is contacted with the catalyst composition in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The process is suitably carried out at a temperature in the range of from 300 to 500° C., a pressure in the range of from 0.1 to 50 bar (10 to 5,000 kPa), using a liquid hourly space velocity of in the range of from 0.5 to 20 $h^{-1}$. A partial pressure of hydrogen in the range of from 0.05 to 30 bar (5 to 3,000 kPa) is generally used. The feed to hydrogen molar ratio is in the range of from 0.5 to 100, generally from 1 to 10 mol/mol.

The present invention will now be illustrated by the following Examples.

EXAMPLES

In the Examples and where mentioned elsewhere hereinabove, the following test methods are applicable:
Flat plate crush strength: ASTM D 6175
Porosity: ASTM D 4284 with drying of the sample at 300° C. for 60 minutes prior to measurement, and using mercury intrusion.
B.E.T. surface area measurement: ASTM D 3663-99, as modified by ISO 9277, with drying of the sample at 300° C. for 60 minutes prior to measurement, and using nitrogen as adsorbate.
Water pore volume: the sample is dried at 300° C. for 1 hour and then weighed; water is added until the pores are filled such that the sample particles are wet but still free flowing; the sample is again weighed and the amount of water absorbed per unit mass is calculated from the two weights.

In the Examples, unless otherwise specified, the zeolites were used in the $H^+$ form and free of template material.

Example 1

Catalyst 1

A carrier was prepared from a large crystallite size zeolite with a ZSM-5 structure with an average crystallite size in the range of from 1 to 10 μm and a silica to alumina bulk ratio of 40 prepared following the procedure of Iwayama et al in U.S. Pat. No. 4,511,547. The zeolite powder was mixed with a low sodium grade silica (Sipernat 50 from Degussa), and an ammonium stabilized commercially available silica sol (sold under the trade name Bindzil by Eka Chemicals), and extruded using 1.5 wt % of ammonium hydroxide solution (containing 25 wt % ammonia) on dry basis to give a carrier comprised of 40 wt % zeolite, 40 wt % Sipernat 50 and 20 wt % silica sol on dry basis.

The green extrudates were dried and calcined above 600° C. for 1 hour to achieve sufficient strength for industrial application.

The resulting carrier had a water pore volume of 0.65 $ml \cdot g^{-1}$. Measured by mercury porosimetry, the catalyst showed 0.55 $ml \cdot g^{-1}$ pore volume, and B.E.T. surface area of 198 $m^2 \cdot g^{-1}$. The flat plate crush strength was 109 $N \cdot cm^{-1}$.

The carrier was pore volume impregnated with a Pt/Sn solution having a pH below 2; the solution was prepared from $H_2PtCl_6$ and $SnCl_2 \cdot 2H_2O$. The concentration of both metals was such as to provide a final catalyst having a Pt/Sn concentration of 0.025/0.4 wt %, based on total catalyst. Once the impregnation was completed, the catalyst was dried at 125° C. for 3½ hours, and subsequently calcined in a two-step calcination program aiming at 480° C. with an intermediate stop at 300° C., and a sufficient low ramping rate to achieve adequate dispersion of the metallic phase. The total calcination procedure lasted 17 hours.

Example 2

Comparative

Catalyst 2

A zeolite identical to that used for Example 1 was used in an alternative carrier preparation where the silica and silica sol was replaced by an alumina powder from Sasol (trade name Pural SB1). The amount of zeolite was left unchanged, so the resulting carrier (after drying and calcination) contained 40 wt % zeolite with the balance being alumina. The carrier was subjected to the pore volume impregnation (utilizing a platinum and tin salt solution prepared as in Example 1), drying and calcining procedures described in Example 1 to yield a final catalyst having a Pt/Sn concentration of 0.025/0.4 wt %, based on total catalyst.

Example 3

Comparative

Catalyst 3

In analogous manner to Example 2, an identical zeolite and an alternative industrial grade alumina, having a higher surface area and pore volume than Pural SB1, was used to prepare a 40 wt % zeolite-containing carrier, with the balance being alumina. This carrier was pore volume impregnated, dried and calcined using the same procedures as in Example 2 to provide a final catalyst composition having the same metals loadings as Examples 1 and 2.

Example 4

Catalyst 1, Catalyst 2, and Catalyst 3 were subjected to a catalytic test that mimics typical industrial application conditions for ethylbenzene dealkylation. This activity test uses an industrial feed of European origin. The composition of the feed used here is summarized in Table 1.

TABLE 1

| Composition of the Feed Used in the Activity Testing Feed composition | | |
|---|---|---|
| EB | wt % | 13.68 |
| pX | wt % | 0.18 |

TABLE 1-continued

Composition of the Feed Used in the Activity Testing
Feed composition

| | | |
|---|---|---|
| oX | wt % | 18.12 |
| mX | wt % | 62.06 |
| toluene | wt % | 0.48 |
| benzene | wt % | 0.13 |
| $C_7$-$C_8$-naphthenes | wt % | 5.35 |
| $C_9^+$ aromatics | wt % | 0.00 |
| Total | wt % | 100.00 |
| $C_8$ aromatics | sum | 94.97 |
| EB in $C_8$ aromatics feed | wt % | 11.25 |
| pX in xylenes in feed | wt % | 0.22 |
| oX in xylenes in feed | wt % | 22.54 |
| mX in xylenes in feed | wt % | 77.23 |

The activity test is performed once the catalyst is in its reduced state, which is achieved by exposing the dried and calcined catalyst to atmospheric hydrogen (>99% purity) at 450° C. for 1 hour.

After reduction the reactor is pressurized without a cooling step, and the feed is introduced. This step contributes to enhanced catalyst aging, and therefore allows comparison of the catalytic performance at stable operation.

The catalytic datapoints are collected at a condition that exaggerates the potential negative operational effects. Therefore, the performance is measured not at the ideal industrial operating condition(s), but at those that allow a better differentiation of the various performance parameters used to evaluate catalysts in this application.

In the present case, a weight hourly space velocity of 4.6 $h^{-1}$, a hydrogen to feed ratio of 2.5 mol·$mol^{-1}$, a total system pressure of 1.3 MPa was used. The temperature was varied between 360 and 410° C. to achieve the required conversion for easier comparison.

The performance characteristics were evaluated as follows:

$$EB \text{ conversion (wt\%)} = \frac{EB_{f.} - EB_{pr.}}{EB_{f.}} \times 100$$

$$\text{Benzene selectivity (mol\%)} = \frac{B_{pr.} - B_{f.}}{EB_{f.} - EB_{pr.}} \times \frac{106}{78} \times 100$$

$$\text{Benzene purity (wt\%)} = \frac{B_{pr.}}{B_{pr.} + cHx_{pr.} + McP_{pr.}} \times 100$$

$$\text{Xylene losses (wt\%)} = \frac{Xyl_{f.} - Xyl_{pr.}}{Xyl_{f.}} \times 100$$

$$\text{Toluene (wt\%)} = \left(\frac{Tol_{pr.}}{\sum \text{product}} - \frac{Tol_{f.}}{\sum \text{feed}}\right) \times 100$$

$$C_9^+ \text{aromatics (wt\%)} = \frac{C_9^+ arom._{pr.}}{\sum \text{product}} \times 100$$

$$\text{Gas make (wt\%)} = \frac{\sum_{i=2}^{5} C_{ipr.}}{\sum \text{product}} \times 100$$

$$pX \text{ ate (\%)} = \frac{pX \text{ in } Xyl_{pr.} - pX \text{ in } Xyl_{f.}}{pX \text{ in } Xyl_{eq.} - pX \text{ in } Xyl_{f.}} \times 100$$

where EB stands for ethylbenzene, B for benzene, Tol for toluene, cHx for cyclohexane, McP for methyl-cyclopentane, Xyl for xylenes in general (all isomers), pX for para-xylene, Cipr for all light hydrocarbons from $C_2$ to $C_5$ in the product, f for feed, and pr for product.

For EB conversion a temperature differential above 2° C. shows a significant improvement in activity; for benzene selectivity above 1 mol % is significant and a reduction in xylene losses of 0.5 or more is a significant improvement. Regarding benzene purity, a purity of 99.8 wt % allows the benzene to be sold directly as a pure product while a stream having less than 99.8 wt % purity has to undergo further purification.

TABLE 2

Temperature Required for 75 wt % Ethylbenzene Conversion,
Benzene Selectivity, Benzene Purity, and Xylene Losses
at 75 wt % Ethylbenzene Conversion (EBC)

| | $T_{req.}$ for 75 wt % EBC ° C. | Benzene selectivity mol % | Benzene purity wt % | Xylene losses wt % |
|---|---|---|---|---|
| Catalyst 1 | 370 | 86.4 | 99.7 | 4.5 |
| Catalyst 2 (comparison) | 368 | 80.9 | 99.8 | 7.4 |
| Catalyst 3 (comparison) | 373 | 79.7 | 99.9 | 6.7 |

In all test runs, xylene isomerisation also occurred and in each case the content of p-xylene reached a minimum of 98% of its equilibrium value.

Table 2 shows the dramatic difference between the use of catalysts having silica- and alumina-bound carriers at identical metal loadings. The benzene selectivity is much higher with the silica-bound carrier version and the xylene losses are significantly lower.

Benzene purity for all catalysts is very high, being in the vicinity of 100 wt %, indicating the very good selectivity of the Pt/Sn metallic phase towards olefin hydrogenation instead of the saturation of the aromatic ring containing molecules. The temperature required for 75 wt % ethylbenzene conversion are similar showing that the overall activity of these catalysts for dealkylation are closely comparable.

Example 5

Catalyst 4

A catalyst carrier was prepared following the preparation route described in Example 1, but with a modification in zeolite content. In this case the zeolite content was set to 25 wt % in the carrier. The silica content of the carrier was 75 wt % and was made up of silica (Sipernat 50) and silica sol (Bindzil) in a weight ratio of 2:1. The flat plate crush strength of the carrier was 152 N/cm.

Metal impregnation, drying and calcination procedures were carried out in identical manner to Example 1.

Example 6

Comparative

Catalyst 5

A carrier was prepared by following the procedures of Example 5 and using the same zeolite and silica starting materials. The resulting carrier was pore volume impregnated with a Pt containing solution having a pH close to neutral. The solution was prepared from $Pt(NH_3)_4(OH)_2$, and contained added ammonium nitrate in an amount sufficient to increase the ionic strength of the solution to be comparable with that of Example 5. This was considered necessary to ensure that there was a corresponding salt content present to that of the Pt/Sn impregnation solution used in Example 5. The concentration of the solution was adjusted so that the final catalyst contained 200 ppmw Pt (0.02 wt % Pt).

Drying and calcination of the pore volume impregnated catalyst was carried out as described in Example 1.

Example 7

Samples of Catalysts 1, 4 and 5 were subjected to the activity test described in Example 4 using the same feed. The key performance parameters are listed in Table 3, and compared at 75 wt % ethylbenzene conversion level.

TABLE 3

Temperature Required for 75 wt % Ethylbenzene Conversion, Benzene Selectivity, Benzene Purity, and Xylene Losses at 75 wt % Ethylbenzene Conversion (EBC)

|  | $T_{req.}$ for 75 wt % EBC °C. | Benzene selectivity mol % | Benzene purity wt % | Xylene losses wt % |
|---|---|---|---|---|
| Catalyst 1 | 370 | 86.4 | 99.7 | 4.5 |
| Catalyst 4 | 392 | 95.5 | 99.8 | 3.0 |
| Catalyst 5 (comparison) | 376 | 85.4 | 97.3 | 3.6 |

In each run, p-xylene was produced in an amount which was a minimum of 98% of its equilibrium value.

The data in Table 3 clearly demonstrate the advantages of reducing the zeolite content in the carrier from 40 wt % to 25 wt % (Catalyst 1 compared with Catalyst 4). The benzene selectivity, and the xylene losses improve significantly at identical ethylbenzene conversion; however the temperature required for 75 wt % ethylbenzene conversion also increases.

Additionally, the comparison of Catalyst 4 and Catalyst 5 shows a similar effect between the two 25 wt % zeolite-containing systems, where the metallic phase is different. Catalyst 4, having a Pt/Sn formulation, has a lower activity, but compensates for this with a very good benzene selectivity, benzene purity, and low xylene losses. The Pt-only catalyst, Catalyst 5, has almost as high an activity as Catalyst 1, but suffers from lower selectivity, lower purity and higher xylene losses compared to its Pt/Sn counterpart. It is noted that the platinum of Catalyst 5 is present in slightly reduced amount to that of Catalyst 1, but the difference (0.005 wt %) is insignificant and will not influence the results given.

Example 8

Catalyst 6

A carrier was prepared following the procedures of Example 1. All ingredients were identical, with the exception of the silica component; this was replaced with a modified version of Sipernat 50, commercially available as Sipernat 500LS from Degussa, where the powder has been milled to a mean particle size in the range of from 2 to 10 μm to remove the large agglomerates of particles. The zeolite content was reduced to 25 wt %; the silica/silica sol content of the carrier was 75 wt %; again the silica/silica sol was used in a weight ratio of 2:1.

The carrier obtained showed remarkable increase in flat plate crush strength, improving it to 191 N·cm$^{-1}$, while the other physical parameters were close to those measured for Catalyst 1. The water pore volume remained at 0.65 ml·g$^{-1}$, the pore volume from the mercury porosimetry was also identical at 0.55 ml·g$^{-1}$, while the B.E.T. surface area increased to 253 m$^2$·g$^{-1}$.

Example 9

Catalyst 7

A carrier was prepared following the procedures described in Example 5, with replacement of the zeolite by a small particle size version of ZSM-5 having a primary particle diameter below 200 nm, and a silica to alumina bulk ratio of 30 (available under the trade name CBV 3020E from Zeolyst International). The carrier obtained was formed of 25 wt % zeolite and 75 wt % silica and had a flat plate crush strength of 123 N/cm.

The catalyst was prepared by impregnating the above carrier with platinum and tin following the preparation recipe of Example 1 to give a catalyst having 0.025 wt % Pt and 0.4 wt % Sn.

Example 10

Catalyst 8

Part of the carrier obtained as described in Example 9 was subjected to the surface modification procedure described in Example 1 of U.S. Pat. No. 6,949,181 B2. The concentration of the ammonium hexa-fluorosilicate was set at 0.02 M. Subsequently, the carrier was washed and dried at 500° C.

The carrier was then impregnated with a Pt/Sn solution, dried and calcined as described in Example 1 to give a catalyst having 0.025 wt % Pt and 0.4 wt % Sn.

Example 11

Catalyst samples prepared in Example 9 and Example 10 were tested according to the procedure and test conditions described in Example 4. The key performance parameters are listed in Table 4, and compared at 75 wt % ethylbenzene conversion level.

TABLE 4

Temperature Required for 75 wt % Ethylbenzene Conversion, Benzene Selectivity, Benzene Purity, and Xylene Losses at 75 wt % Ethylbenzene Conversion (EBC)

|  | $T_{req.}$ for 75 wt % EBC °C. | Benzene selectivity mol % | Benzene purity wt % | Xylene losses wt % |
|---|---|---|---|---|
| Catalyst 7 | 396 | 91.4 | 99.9 | 6.0 |
| Catalyst 8 | 405 | 97.7 | 99.7 | 3.2 |

In each run p-xylene was produced in an amount which was a minimum of 98% of its equilibrium value.

It is clear that the surface modification dramatically alters the benzene selectivity and the xylene losses. The temperature required for 75 wt % ethylbenzene conversion is however also increased slightly. The selectivity pattern of the treated catalyst is very attractive: the xylene losses are almost halved, while the benzene purity is retained. The benzene selectivity is increased to close to 100 mol %.

Example 12

Catalyst 9

A catalyst carrier was prepared following the procedures described in Example 1, with the zeolite replaced by the alternative ZSM-5 zeolite of Example 9. This zeolite grade was used in ammonium form, and did not contain any template material. The zeolite content was 40 wt % and the total silica content (w/w silica:silica sol, 2:1) was 60 wt %. The carrier exhibited a flat plate crush strength of 117 N/cm.

The carrier was subject to a surface modification step following Example 1 of U.S. Pat. No. 6,949,181 B2. The concentration of the ammonium hexafluorosilicate was set at 0.02 M.

The metal impregnation step, and subsequent drying and calcination steps, were identical to those described in Example 1. The final catalyst had a platinum content of 0.025 wt % and a tin content of 0.4 wt %. The calcination converted the ammonium form zeolite into the $H^+$ form.

Example 13

Catalyst 10

A carrier was prepared according to Example 12, with the ZSM-5 grade used in its template-containing version. All other preparation steps were identical. The carrier contained 40 wt % zeolite and 60 wt % silica (w/w silica:silica sol, 2:1); the final catalyst had a metals loading of 0.025 wt % Pt and 0.4 wt % Sn. Before the surface modification treatment, the carrier had a flat plate crush strength of 82 N/cm; after the treatment the strength had increased to 104 N/cm.

Catalyst 11

For this catalyst, the procedure used for Catalyst 10 was followed but, before the metal impregnation step, the carrier (with template-containing ZSM-5) was subjected to a second surface modification step. All other preparation steps were the same as described in Example 12. The subsequent metal impregnation was identical to that carried out for Catalyst 10. The carrier again had a content of 40 wt % zeolite and 60 wt % silica (w/w silica:silica sol, 2:1); the final catalyst had a metals loading of 0.025 wt % Pt and 0.4 wt % Sn.

Catalyst 12

In addition, a third variation of this carrier was prepared, where the concentration of the active agent in the surface modification step was doubled. All additional preparation steps remained identical. The carrier again had a content of 40 wt % zeolite and 60 wt % silica (w/w silica:silica sol, 2:1); the final catalyst had a metals loading of 0.025 wt % Pt and 0.4 wt % Sn.

Example 14

Catalyst 13

A carrier was prepared following the procedures described in Example 12, including the surface modification treatment, with the zeolite replaced by a ZSM-5 having a silica to alumina bulk ratio of 80 and a primary particle size of 30 to 100 nm. The zeolite content of the carrier was increased to 60 wt %. All other preparation steps were carried out as described in Example 12. The carrier had a content of 60 wt % zeolite and 40 wt % silica (w/w silica:silica sol, 3:1); the final catalyst had a metals loading of 0.025 wt % Pt and 0.4 wt % Sn. Prior to the surface modification treatment, the carrier had a flat plate crush strength of 53 N/cm, which is not adequate for industrial applications. After the surface modification treatment, the flat plate crush strength had increased to 69 $N \cdot cm^{-1}$, which is acceptable for commercial use.

Example 15

Catalysts 9, 10, 11, 12, and 13 were tested in the catalytic activity test described in Example 4. The results were compared at 50 wt % ethylbenzene conversion level, and are given in Table 5.

TABLE 5

Temperature Required for 50 wt % Ethylbenzene Conversion, Benzene Selectivity, Benzene Purity, and Xylene Losses at 50 wt % Ethylbenzene Conversion (EBC)

|  | $T_{req.}$ for 50 wt % EBC ° C. | Benzene selectivity mol % | Benzene purity wt % | Xylene losses wt % |
|---|---|---|---|---|
| Catalyst 9 | 358 | 91.2 | 99.8 | 2.4 |
| Catalyst 10 | 360 | 92.6 | 99.8 | 1.7 |
| Catalyst 11 | 371 | 91.2 | 99.8 | 2.0 |
| Catalyst 12 | 353 | 92.4 | 99.7 | 2.6 |
| Catalyst 13 | 350 | 93.1 | 99.7 | 1.5 |

In each run p-xylene was produced in an amount which was a minimum of 98% of its equilibrium value.

Table 5 demonstrates that little difference can be found in the activity or performance for benzene selectivity of the final catalyst prepared from a template-free or a template-containing zeolite in ethylbenzene dealkylation. The template-containing zeolitic catalysts did however yield lower xylene losses.

Increasing the severity of the surface moderation step by repeating the process (Catalyst 11) does not bring a noticeable improvement in the overall selectivity, while it negatively affects the activity of the catalyst, (shown as a higher temperature required for an identical conversion level). Increasing the concentration of the active agent during the surface moderation procedure (Catalyst 12) resulted in a more active catalyst, though the xylene losses were not improved compared to Catalyst 10.

The catalyst based on the higher silica to alumina ratio zeolite (Catalyst 13) showed a very attractive performance, but it must be noted that the zeolite amount had to be increased to ensure a good activity, and the strength of the carrier without surface modification was unsatisfactory for commercial application.

Example 16

Catalyst 14

A catalyst was prepared following the procedures described in Example 1 and using the same zeolite and silica starting materials in the same quantities, but where the Pt/Sn solution was neutralized: in order to prevent precipitation of the metals, a complexing agent, EDTA was added to the solution. A stable solution could be achieved at an EDTA/Sn molar ratio of 2. Using this solution, the carrier was impregnated with platinum and tin to achieve identical metal loadings as in Example 1. The green extrudates were dried and calcined to obtain the final catalyst.

Example 17

Two catalysts were prepared following Example 1, where the amount of ammonia added during the extrusion as a peptization aid was varied. A dramatic difference in the pore structure of the resulting carrier was observed. The carrier extrudates were turned into a final catalyst as described in Example 1.

Two sample carriers were prepared following the procedure of Example 1. For Sample no. 1, 1.6 wt % NH$_4$OH solution (containing 25 wt % ammonia) on dry basis was added for extrusion. For Sample no. 2, 2.0 wt % of the same NH$_4$OH solution was added to the solids. For each Sample catalysts were prepared using the same metals in the same amounts as in Example 1.

A catalytic test was performed following the activity test of Example 4 and using the same feed. The porosity data and the catalytic results are provided in Table 6.

TABLE 6

Physical Properties and the Catalytic Performance Details of Two Samples Prepared with Varying Amount of ammonia Used in the Extrusion Step

|  | Sample no. 1 | Sample no. 2 |
|---|---|---|
| H$_2$O PV (ml · g$^{-1}$) | 0.87 | 0.63 |
| Hg PV (ml · g$^{-1}$) | 0.78 | 0.53 |
| Hg SA (m$^2$ · g$^{-1}$) | 201 | 200 |
| MPoD(V) (nm) | 20.3 | 11.5 |
| T$_{req.}$ for 75 wt % EBC (° C.) | 361.8 | 367.6 |
| Benzene selectivity (mol %) | 81.1 | 84.3 |
| Benzene purity (wt %) | 99.6 | 99.8 |
| Xylene losses (wt %) | 6.8 | 5.6 |

In each run p-xylene was produced in an amount which was a minimum of 98% of its equilibrium value.

While the surface area of the carrier did not change, the pore volume (measured by water or mercury porosimetry) is increased substantially after the high NH$_3$ extrusion, and the medium pore diameter almost doubled, all indicating a dramatic shift in the porosity.

The temperature required for 75 wt % EB conversion for the catalyst stemming from the "high NH$_3$" extrudates (Sample no. 2) was ~5° C. higher than that prepared from Sample no. 1, which denotes a lower activity, and the benzene selectivity was also lower, mainly because the xylene losses have increased by more than 1 wt %. The benzene purity, related to the applied metallic phase, has not decreased significantly.

What is claimed is:

1. A catalyst composition which comprises:
a surface-modified carrier, wherein the surface-modified carrier comprises a carrier that has been subjected to a dealumination treatment by contacting the carrier with either an aqueous solution of fluorosilicate salt of the formula (A)$_{2/b}$ SiF$_6$, wherein A is a metallic or non-metallic cation other than H$^+$ having valence b and b is the valence of A, or an aqueous solution of hexafluorosilicate salt or dicarboxylic acid, wherein the carrier comprises from 30 wt % to 80 wt % of a silica binder comprising a powder form silica and a silica sol in a weight ratio of powder form to sol in the range of from 1:1 to 10:1; and 20 wt % to 70 wt % of a pentasil zeolite, having an average crystallite size in the range of from 1 to 10 µm and a bulk silica to alumina ratio in the range of from 20 to 150 and being in its H$^+$ form, with all percentages being on the basis of total carrier and, wherein the dealumination treatment provides a dealumination ratio in the range of from 1.1 to 3.0; and
platinum in an amount in the range of from 0.001 to 0.1 wt %, on the basis of total catalyst; and
tin in an amount in the range of from 0.01 to 0.5 wt %, on the basis of total catalyst.

2. The catalyst composition as claimed in claim 1, wherein the carrier is composed of in the range of from 30 to 80 wt % silica, and in the range of from 20 to 70 wt % zeolite.

3. The catalyst composition as claimed in claim 2, wherein the dealumination treatment of the carrier includes subjecting the carrier to a dealumination treatment with ammonium hexafluorosilicate.

4. The catalyst composition as claimed in claim 3, wherein the pentasil zeolite is one having an MFI configuration.

5. The catalyst composition as claimed in claim 4, wherein the zeolite having the MFI configuration is ZSM-5.

6. The catalyst composition as claimed in claim 5, wherein the ZSM-5 has a SAR in the range of from 20 to 50 and is present in the carrier in an amount in the range of from 20 to 50 wt %.

7. The catalyst composition as claimed in claim 6, wherein the silica has a mean particle size in the range of from 2 to 60 µm.

8. A catalyst composition, comprising:
a carrier comprising from 30 to 80 wt % of a dealuminated pentasil zeolite, wherein the dealuminated pentasil zeolite is prepared with a starting pentasil zeolite having an average crystallite size in the range of from 1 to 10 µm and a SAR in the range of from 20 to 150 that has been dealuminated to a dealumination ratio in the range of from 1.1 to 3.0, and from 20 to 70 wt % silica binder, comprising a mixture of a powder form silica and a silica sol in a weight ration of powder form to sol in the range of from 1:1 to 10:1 with the weight percentages being based on the total carrier;
a platinum component in an amount in the range of from 0.001 to 0.1 wt %, based on the total catalyst; and
a tin component in an amount in the range of from 0.01 to 0.5 wt %, based on the total catalyst.

9. A catalyst composition as recited in claim 8, wherein said carrier comprises from 30 to 50 wt % of said dealuminated pentasil zeolite and from 50 to 70 wt % of said silica binder.

10. A catalyst composition as recited in claim 8, wherein the pentasil zeolite of said dealuminated pentasil zeolite is of the type having an MFI configuration.

11. A catalyst composition as recited in claim 8, wherein the dealuminated pentasil zeolite is surface dealuminated by subjecting the pentasil zeolite of said dealuminated pentasil zeolite to a dealumination treatment with ammonium hexafluorosilicate.

12. A catalyst composition as recited in claim 8, wherein said pentasil zeolite is ZSM-5.

13. A catalyst composition as recited in claim 8, wherein said dealumination ratio is in the range of from 1.3 to 2.5.

14. A catalyst composition, comprising:
a surface-modified carrier, wherein said surface-modified carrier comprises a carrier that has been subjected to a dealumination treatment by contacting said carrier with either an aqueous solution of fluorosilicate salt of the formula (A)$_{2/b}$SiF$_6$, wherein A is a metallic or non-metallic cation other than H$^+$ having valence b and b is the valence of A, or an aqueous solution of hexafluorosilicate salt or dicarboxylic acid, wherein said carrier comprises from 20 to 70 wt % of a pentasil zeolite, having an average crystallite size in the range of from 1 to 10 µm, that has not been subjected to said dealumination treatment of said carrier and from 30 to 80 wt % silica binder, comprising a mixture of a powder form silica and a silica sol in a weight ratio of powder form to sol in the range of from 1:1 to 10:1, with the weight percentages being based on the total carrier, and wherein said dealumination treatment provides for a dealumination ratio in the range of from 1.1 to 3.0.

a platinum component in an amount in the range of from 0.001 to 0.1 wt %, based on the total catalyst; and a tin component in an amount in the range of from 0.01 to 0.5 wt %, based on the total catalyst.

15. A catalyst composition as recited in claim 14, wherein said carrier comprises from 30 to 50 wt % of said non-surface modified pentasil zeolite and from 50 to 70 wt % silica.

16. A catalyst composition as recited in claim 14, wherein the pentasil zeolite of said dealuminated pentasil zeolite is of the type having an MFI configuration.

17. A catalyst composition as recited in claim 14, wherein said surface-modified carrier is dealuminated by subjecting the pentasil zeolite of said carrier to a dealumination treatment with ammonium hexafluorosilicate.

18. A catalyst composition as recited in claim 14, wherein said non-surface modified pentasil zeolite is ZSM-5.

* * * * *